United States Patent [19]

Siposs

[11] 4,368,118
[45] * Jan. 11, 1983

[54] BLOOD-AIR SEPARATOR AND FILTER

[76] Inventor: George G. Siposs, 2855 Velasco Lane, Costa Mesa, Calif. 92626

[*] Notice: The portion of the term of this patent subsequent to Aug. 17, 1999, has been disclaimed.

[21] Appl. No.: 186,976

[22] Filed: Sep. 15, 1980

Related U.S. Application Data

[63] Continuation-in-part of Ser. No. 109,801, Jan. 7, 1980, Pat. No. 4,344,777.

[51] Int. Cl.³ ............................................. B01D 19/00
[52] U.S. Cl. ..................................... 210/136; 55/178; 55/201; 210/436; 210/456; 210/927
[58] Field of Search ................. 55/202, 201, 203, 178, 55/206, 52; 210/436, 440, 456, 443, 136, 444, 247, 927

[56] References Cited

U.S. PATENT DOCUMENTS

| | | | |
|---|---|---|---|
| 2,018,901 | 10/1935 | Rush | 55/52 |
| 2,952,330 | 9/1960 | Wihslow | 55/202 |
| 3,242,643 | 3/1966 | Moore et al. | 55/52 X |
| 3,468,614 | 9/1969 | Hilssuh | 55/52 X |
| 4,085,040 | 4/1978 | Egah | 210/456 X |
| 4,164,468 | 8/1979 | Raible | 219/436 X |
| 4,190,426 | 2/1980 | Ruschke | 210/927 X |

FOREIGN PATENT DOCUMENTS 1132313 10/1956 France .............................. 210/436

Primary Examiner—Frank A. Spear, Jr.
Attorney, Agent, or Firm—Allen A. Dicke, Jr.

[57] ABSTRACT

The blood-air separator is for use in the extracorporeal blood bypass during cardio-pulmonary surgery. Air bubbles are separated from the recirculating blood stream by centrifugal force and buoyancy after the stream has left the oxygenator and before it returns to the patient. Separation is accomplished by imparting circular motion to the bloodstream within the separator at a point where air bubbles can move upward and inward, and blood liquid outward and downward. Curved vanes in the blood flow stream cause the circular blood motion.

27 Claims, 6 Drawing Figures

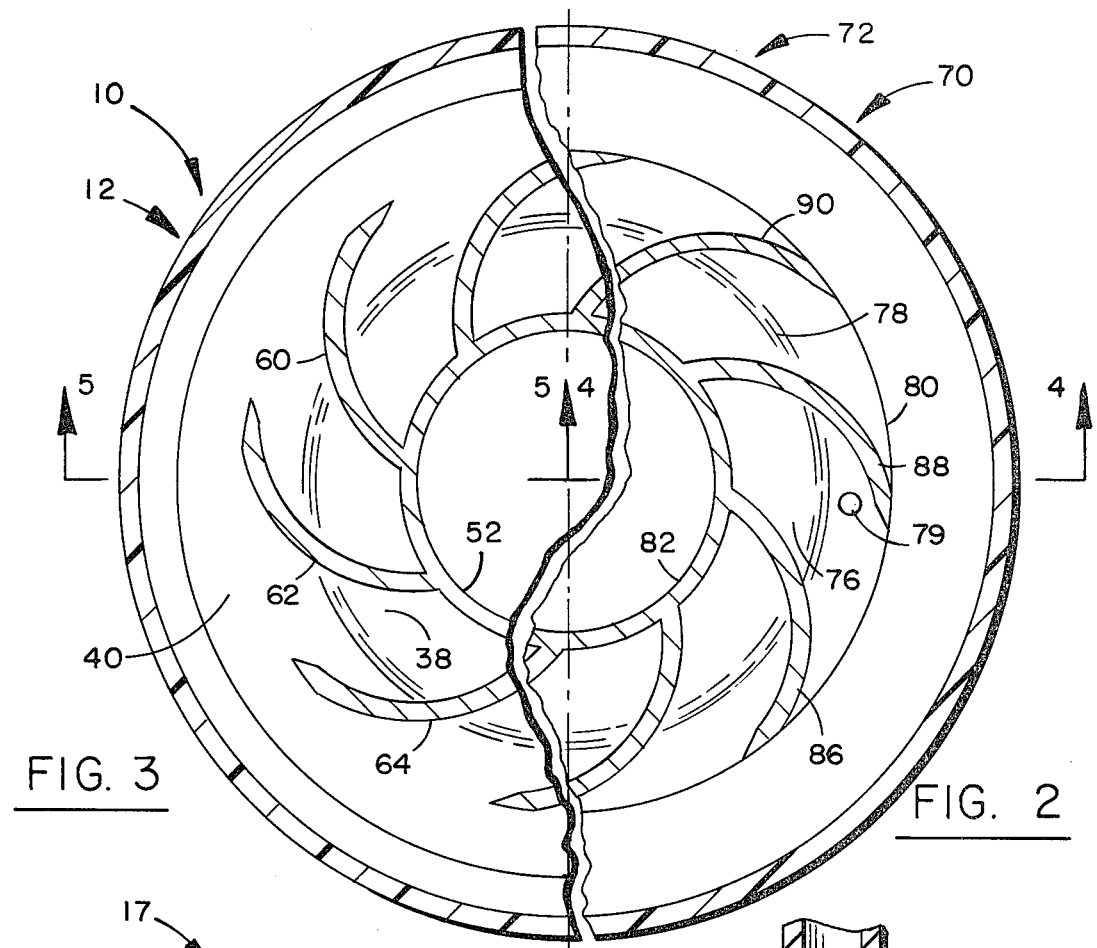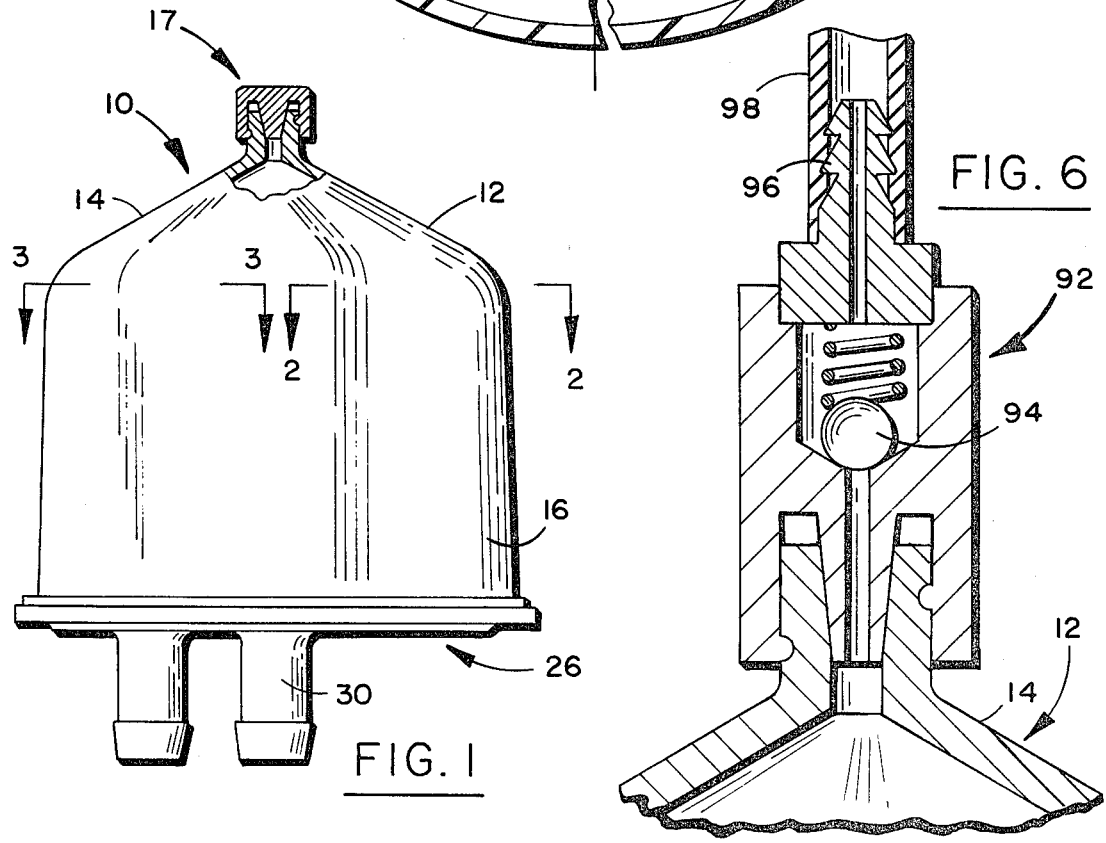

BLOOD-AIR SEPARATOR AND FILTER

CROSS-REFERENCE

This application is a continuation-in-part of patent application Ser. No. 109,801 filed Jan. 7, 1980 by George G. Siposs and entitled "Blood Filter," now U.S. Pat. No. 4,344,777 the entire disclosure of which is incorporated herein by this reference.

BACKGROUND

This invention is directed to a blood-air separator for positioning in the extra-corporeal blood bypass circuits which are used in cardio-pulmonary surgery, particularly in the arterial bloodstream just before it reenters the body.

It is necessary to separate gas bubbles, usually air bubbles, from the arterial bloodstream before the stream returns to the patient. Air embolism can quickly cause death. The blood filters which are sometimes used in the extra-corporeal blood bypass circuit tend to filter out air bubbles because the air bubbles do not readily pass through the blood-wetted filter element. However, from the surface of the filter element, it is hard to permit the bubbles to rise and accumulate in the top of the filter housing so that they can be separated. In conventional filters, some bubbles can be seen to circulate for quite a while, and it is difficult to capture them or permit them to accumulate in the top of the filter because of turbulence of many small bubbles. The prior art filters, except the blood filter described in the above-identified parent application, are not well-designed for the removal of air from the arterial bloodstream. Thus, there is need for a structure which readily and reliably removes air bubbles from the bloodstream.

SUMMARY

In order to aid in the understanding of this invention it can be stated in essentially summary form that it is directed to a blood-air separator which includes a body having an upper air chamber and a lower outlet, with a blood inlet juxtapositioned. The blood inlet is configured to provide a circumferential velocity vector in the blood flow so that air bubbles can combine and move upward while liquid blood moves downward towards the outlet. The separator may include a filter for filtering out small bubbles in the bloodstream as a secondary preventer in the blood outlet stream. The filter may also separate out solid contaminants.

It is, thus, an object of this invention to provide a separator for separating gas bubbles from a flowing blood stream, particularly useful in an extra-corporeal blood flow circuit during cardio-pulmonary bypass so that air bubbles are continuously separated out of the circulating blood. It is another object to separate air bubbles from the flowing bloodstream by centrifugal separation, but with substantially constant velocity through the separator to minimize blood turbulence to minimize hemolysis. It is another object to provide a convenient place in the upper part of the air bubble separator in a position with minimized blood flow to permit air bubbles to congregate and join and a place from which they can be exhausted. It is a further object to provide an air separator for a cardio-pulmonary bypass circuit wherein both the inlet and outlet connections are downwardly directed on the bottom of the separator so that inlet and outlet tubes can be connected thereto to eliminate buckled lines and provide convenient, short connections. It is a further object to provide such a separator which has a minimum volume to minimize the volume of blood required to prime the lines and the air separator. It is a further object to provide such an air separator which also has a filter therein for final filtration of air bubbles and for filtration of particulate contaminants from the bloodstream.

Other objects and advantages of this invention will become apparent from a study of the following portion of the specification, the claims and the attached drawings.

BRIEF DESCRIPTION OF THE DRAWINGS

FIG. 1 is a side-elevational outside view of the blood-air separator of this invention.

FIG. 2 is an enlarged partial section looking downwardly through the separator body, showing it in the embodiment in which a filter is not employed, seen generally along the line 2—2 of FIG. 1.

FIG. 3 is a downwardly looking section through the body of the separator of this invention in the embodiment wherein a particulate filter is employed, with parts broken away, as generally seen along the line 3—3 of FIG. 2.

FIG. 6 is a section through an alternate air outlet from the separator body.

BRIEF DESCRIPTION OF THE PREFERRED EMBODIMENTS

Figures 4, 5:
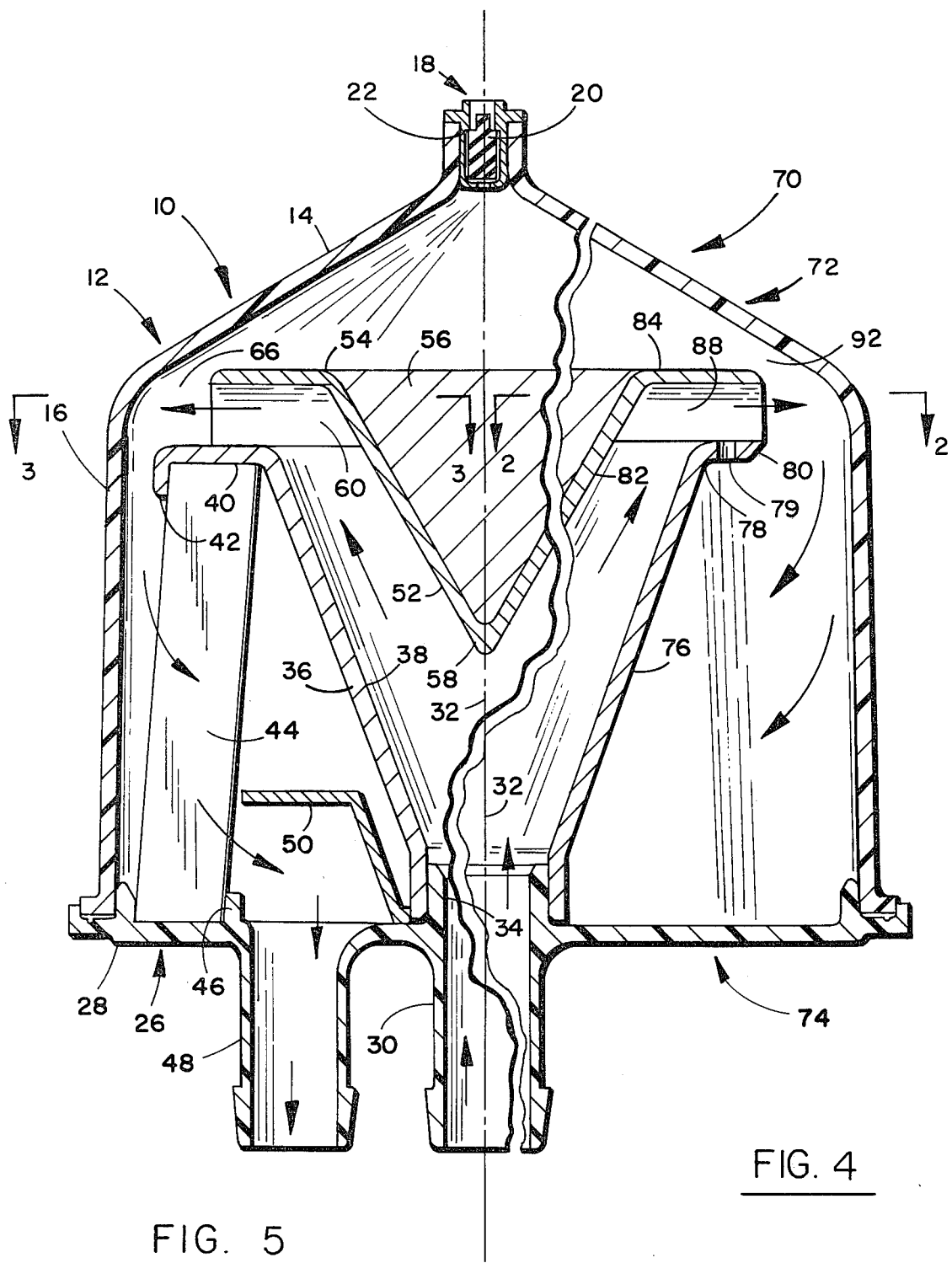
FIG. 4 is a vertical section through the body, with parts broken away, generally seen along the line 4—4 of FIG. 2.
FIG. 5 is a vertical section through the body, taken generally along the line 5—5 of FIG. 3.

The first preferred embodiment of the blood-gas separator of this invention is generally indicated at 10 in FIGS. 1, 3 and 5. As will be developed as the description proceeds, this separator 10, in addition to structure which provides blood-gas separation, also includes a filter which removes particulate contaminants from the liquid blood flow stream. Separator 10 has an upper bell-shaped housing 12, with a generally conical top portion 14 and an almost cylindrical lower portion 16. The lower portion is sufficiently conical to permit it to be easily withdrawn from an injection molding die. Separated gas, mostly air, accumulates within top portion 14. Release of the accumulated gas, usually air, can be accomplished in any convenient way. Luer valve 17 is shown in FIG. 1. The Luer valve is conventional in the art and is a screw cap with a built-in tapered plug. In FIG. 5, release valve 18 is provided to permit the discharge of the accumulated gas. Release valve 18, see FIG. 5, is a check valve, with a resilient plug 20 engaging against valve shoulder 22. There is clearance around the sides and bottoms of resilient plug 20 so that its engagement against shoulder 22 provides the sealing area. When the proper tool is inserted down into the open top of release valve 18, it resiliently presses plug 20 away from its sealing shoulder 22 to release the gas within upper housing 12. The tool may be a hypodermic syringe, but any other convenient tool may be used.

FIG. 6 shows gas release valve 92 attached to the male Luer fitting on the top of housing 12. Valve 92 has a check ball 94 in its body and outlet tube fitting 96. Tube 98 on fitting 96 can carry the air bubbles away. Connection to the top of the oxygenator, where the blood is foamed, is suitable disposition for the release of the air and recirculation of the blood. The check valve 94 prevents air return, should the pressure in the separator 10 fall below atmospheric. Instead of a ball check, other types of check valves can be used. A molded duckbill valve or flapper valve are useful in that installation.

Upper housing 12 is the same for both embodiments shown in FIGS. 4 and 5. Lower housing 26 is slightly different in the two embodiments, but comprises bottom plate 28 which seals against the lower edge of lower portion 16 to enclose separator 10. Inlet tube fitting 30 is centrally located on the axis 32 and is a conventional barbed fitting. It is important to the present structure that inlet tube fitting 30 be downwardly directed, as illustrated in FIGS. 1, 4 and 5. Within bottom plate 28, in line with and a part of the inlet structure, is circular boss 34, formed as a part of lower housing 26. Flow cone 36 is secured on circular boss 34, such as by adhesive solvent attachment, ultrasonic welding, or thermoplastic bonding. Flow cone 36 has an interior conical surface 38 which permits the incoming liquid blood flow entering upward through inlet tube fitting 30 to decrease in velocity, due to the increasing area. Interior conical surface 38 is a conical surface of revolution around axis 32. Flange 40, with its downwardly directed outer lip 42 terminates the top of the structure of flow cone 36. Flange 40 is transversely directed. Outer lip 42 is provided to engage around the upper, outer corner of filter 44, which is provided to separate particulate matter out of the flowing blood.

Filter 44 is a suitable filter screen material and corrugated into the truncated conical configuration shown. The filter medium itself is defined in more detail in the parent application referred to above, but is preferably a thermoplastic polymer composition material, such as nylon, which is woven from filaments in the 20 to 60 micron diameter range and provides openings in the range of 20 to 60 microns. The woven filaments may be thermoplastically joined at their points of contact. The fabric may be either square or a twill weave, providing uniformly arranged open areas. Alternatively, a molded micro-porous complex having omidirectional interconnecting openings of 20 to 60 microns made from a polymer composite material (such as polyethylene which is hydrophobic) may be used. The corrugated filter fabric medium 44 is engaged on the top of bottom plate 28 inside of circular flange 46. Filter 44 is preferably sealed both top and bottom against its end flanges and lips in potting compound or the like, to prevent liquid bypass.

Outlet fitting 48 extends downwardly out of bottom plate 28 and is preferaly a barbed fitting. It is positioned inwardly of circular flange 46 so that the liquid available to outlet fitting 48 is filtered. It is important that outlet fitting 48 be downwardly directed so that the connection hoses to separator 10, both inlet and outlet, can drape naturally downward to prevent kinks. Anti-vortex baffle 50 is positioned over the interior opening of outlet fitting 48 to prevent withdrawal of anything but liquid until the liquid supply is low within separator 10. Otherwise, at low liquid levels within the interior of upper housing 12, vortexing may cause the introduction of air into the outlet flow through outlet fitting 48. Anti-vortex baffle 50 thus serves as a further protection against air entrainment in the outlet blood flow stream.

Central cone 52 extends downwardly interiorly of flow cone 36 and is supported on plate 54. As is seen in FIG. 6, central cone 52 may be integrally formed with plate 54, and the interior of cone 52 is preferably filled, either solidly with filler material 56 as shown, or may have a cover plate thereon. Central cone 52 has a larger conical angle with respect to axis 32 than does cone 36. The angle of central cone 52 is chosen so that above the point 58 of the central cone, the cross-sectional area of the flow volume between the cones remains substantially constant so that above point 58, the blood flow velocity is substantially constant. This reduces trauma to the blood cells which is sometimes thought to be caused by fluid shear. A plurality of curved vanes is formed on the underside of plate 54 and outward from central cone 52. A plurality of these vanes is shown at 60, 62 and 64 in FIG. 3, and such vanes extend all the way around the circular opening between transverse flange 40 and plate 54. As is seen in FIG. 3, the vanes are directed so as to cause a circumferential vector in the blood flow to produce a centrifugal force which aids in separating entrained air from the liquid blood. The heavier material, the liquid blood, is thrust radially outward with a greater force than the lower density entrained air. Furthermore, the gravitational effects cause the entrained air to rise up through the air discharge channel 66 between the upper, outer corner of plate 54 and the lower surface of the upper housing adjacent thereto.

The centrifugal action tends to keep the flow horizontal for a longer time than would be the case if the blood merely spilled over and down over lips 42 or 80. Thus, there is more time for bubbles to rise and not be swept down.

As the bubbles rise quietly they converge. If they were turbulent, they would be fragmented. The quiet area above the vanes permits the bubbles to collect out of the main flow stream. By imparting a circular motion to the bloodstream within the separator at a point where air bubbles can move upwardly and inwardly, combining of the tiny air bubbles and separation thereof is effectively accomplished.

In the preferred embodiment, the vanes are circular curves because such are easily accomplished in a molding operation. However, other spiral configurations are suitable. With the comining of the tiny air bubbles and their upward movement through air discharge channel 66, they accumulate under release valve 18 whence they can be released from time-to-time. Upper housing 12 is preferably transparent so that the accumulation of air bubbles can be observed and the accumulated bolus released. Furthermore, with such transparence, the charging of a system with blood can be observed.

FIGS. 2 and 4 illustrate the second preferred embodiment of the separator, indicated generally at 70. Separator 70 is very similar to the separator 10 and incorporates many of the same components. Separator 70 is the same as separator 10, except for the absence of a filter, such as filter 44, for screening particulates out of the blood flow stream. Upper housing 72 is the same as upper housing 12. Lower housing 74 is the same as lower housing 26, except for the absence of circular flange 46 required as bottom securement for filter 44. Flow cone 76 is the same as flow cone 36, except that its upper transverse flange 78 is chamfered at 80, may not extend as far radially outward as flange 40, and may not have the downwardly directed outer lip 42 which is necessary for attachment with the upper edge of filter 44. If there was a lip, air could be trapped under it during priming. To avoid such air trapping, hole 79 can be drilled through the flange. However, when different moldings are employed, they are preferably configured as shown in FIGS. 4 and 5.

Central cone 82 is the same as central cone 52 and carries under its top plate 84 a series of spiral vanes such as vanes 86, 88 and 90, see FIG. 2. The vanes can be spiral or of circular configuration to impart a circumferential vector to the blood flowing outward between flange 78 and plate 84. The centrifugal force imparted by this circular vector provides centrifugal force which aids in providing more non-turbulent separating time. The blood flows downward towards the outlet fitting which is downwardly directed out of lower housing 74, while air bubbles move upward through air discharge channel 92 to conglomerate and accumulate with the inner top of upper housing 72 so that air can be released as required through the previously described release valve. Thus, the separator 70 is just as effective in its conglomeration of tiny air bubbles into larger bubbles as separator 10. However, it must be noted that in addition to the filtration out of particulate contaminants in the bloodstream, filter 44 also aids in preventing through-flow of air bubbles. When a filter fabric of the type described above is wetted with blood, surface tension forces resist the passage through the fabric of air bubbles. The filter fabric thus stops the bubbles in the flow stream until a certain pressure drop across the fabric is reached. This is called the "bubble point." The filter is designed so that, in normal operation, the bubble point is not reached so that the filter itself provides the secondary protection for preventing air bubble flow out of the filter.

The present structure separates the bubbles out of the flowing bloodstream phase, with the natural upward buoyancy of the bubbles enhanced by the centrifugal force. The structure agglomerates the small bubbles until a large, quiet bubble is formed in the upper housing. This bolus of air can be readily released as previously described. Thus, the separators 10 and 70 provide a structure wherein the small bubbles are agglomerated and the resultant large, quiet bubble can be released. In addition, the separator 10 provides additional protection against air in the blood flow stream by means of the bubble point protection provided by the filter 44.

This invention has been described in its presently contemplated best mode and it is clear that it is susceptible to numerous modifications modes and embodiments within the ability of those skilled in the art and without the exercise of the inventive faculty. Accordingly, the scope of this invention is defined by the scope of the following claims.

What is claimed is:

1. An arterial block-gas separator and filter comprising:
   a hollow body, said hollow body having an inlet and an outlet;
   a stationary upwardly divergent flow control member within said body and connected to receive flow through said inlet for causing a reduction in flow velocity as the arterial blood flows upward in said upwardly divergent flow control member to fill said hollow body with arterial blood to a level above said upwardly divergent flow control member;
   blood flow direction control means above said divergent flow control member comprising spirally and circumferentially directed vanes for receiving arterial blood therefrom and to radially and circumferentially direct arterial blood flow within the arterial blood substantially filling said body;
   a chamber within said body above said blood flow direction control means to receive gas separated from the blood flow;
   a blood filter member having an inlet side and an outlet side, said blood filter member being positioned within said hollow body so that its inlet side is towards said chamber and its inlet side receives blood which has already passed through said blood flow direction control means; and
   an outlet from said body below said flow direction control means to receive blood from the outlet side of said filter and to discharge arterial blood with reduced gas content from said separator.

2. The blood-gas separator of claim 1 wherein said vanes are curved vanes.

3. The blood-gas separator of claim 2 wherein said curved vanes are spiral vanes.

4. The blood-gas separator of claim 1 wherein an anti-vortex plate is positioned interiorly of said body and over said outlet to inhibit vortex formation in blood flowing out of said outlet.

5. An arterial blood-gas separator comprising:
   a hollow body, said hollow body having an inlet for permitting the inflow of arterial blood into said body to substantially fill said body and said body having an outlet;
   a stationary upwardly divergent flow control member positioned within said body below the blood level in said body and connected to said inlet to receive arterial blood flow through said inlet for causing a reduction in flow velocity as the arterial blood flows upward in said upwardly divergent flow control member to substantially fill the interior of said hollow body;
   blood flow direction control means above said divergent flow control member for receiving arterial blood therefrom, said blood flow direction control means comprising a plurality of flow deflecting vanes that convert the generally axially directed blood flow upward in said divergent flow control member to tangential flow to phase-separate gases from the blood with the generally tangential flow of the arterial blood being submerged in the substantially arterial blood filled hollow body;
   a chamber within said body above said blood flow control direction control means to receive gas separated from arterial blood flow;
   a blood filter member having an inlet side and an outlet side, said blood filter member being positioned within said hollow body so that its inlet side is towards said chamber and its inlet side receives blood which has already passed through said blood flow direction control means; and
   an outlet from said body below said flow direction control means and on the outlet side of said filter to discharge arterial blood with reduced gas content from said separator.

6. The blood-gas separator of claim 5 wherein said flow deflectors are curved vanes.

7. The blood-gas separator of claim 6 wherein said curved vanes are spiral vanes.

8. An arterial blood-gas separator comprising:
   a hollow body having a central axis, said hollow body having an inlet and an outlet;
   an upwardly divergent flow control member fixed within said body and connected to said inlet to receive arterial blood flow through said inlet, said divergent flow control member being conical about said axis;

a flange at the top of said conical flow control member positioned so that arterial blood delivered by said conical flow control member passes across said flange, said flange being positioned substantially normal to said axis;

blood flow direction control means on said flange and above said conical divergent flow control member for receiving arterial blood therefrom comprising a plurality of vanes, said vanes being shaped to radially and circumferentially direct arterial blood flow within said body so that the arterial blood substantially fills said body;

a chamber within said body above said blood flow control direction control means to receive gas separated from arterial blood flow, a vent valve to vent gas out of chamber;

a blood filter member having an inlet side and an outlet side, said blood filter member being positioned within said hollow body so that its inlet side is towards said chamber and its inlet side receives blood which has already passed through said blood flow direction control means; and an outlet from said body on the outlet side of said filter and below said flow direction control means to discharge arterial blood with reduced gas content from said separator.

9. The blood-gas separator of claim 8 wherein a conical diverter is positioned within said flow control member to direct upward blood flow so that it has some radial flow direction component.

10. The blood-gas separator of claim 9 wherein said conical flow control member and said conical diverter are dimensioned so that cross-sectional area between the interior of said conical flow control member and said conical diverter is substantially constant at different positions along said flow path.

11. The blood-gas separator of claim 9 wherein said conical diverter has a radially directed flange thereon and said blood flow direction control means comprises a plurality of vanes mounted under said flange, said vanes resting on the outlet of said conical flow control member and receiving blood flow therefrom.

12. The blood-gas separator of claim 11 wherein said vanes are curved vanes.

13. The blood-gas separator of claim 12 wherein said conical flow control member also has a radially directed flange thereon, and said curved vanes rest on and are secured to said flange on said conical flow control members.

14. The blood-gas separator of claim 13 wherein a filter is positioned and sealed under said flange on said conical divergent flow control member and over the bottom of said body and around said conical flow member and said outlet from said body so as to filter blood.

15. The blood-gas separator of claim 14 wherein an anti-vortex plate is positioned interiorly of said body and over said outlet to inhibit vortex formation in blood flowing out of said outlet.

16. The blood-gas separator of claim 11 wherein said vanes are spiral vanes.

17. The blood-gas separator of claim 11 wherein a filter is positioned within said body between said flow direction control means and said outlet so as to filter air bubbles and contaminants out of blood flow which is passing to said outlet from said body after centrifugal separation of gas from the blood flow.

18. An arterial blood-gas separator comprising:
a hollow body having a central axis, said hollow body having an inlet and an outlet;

a stationary upwrdly divergent flow control member positioned within said body and connected to said inlet to receive arterial blood flow through said inlet, said divergent flow control member being conical about said axis;

a flange positioned adjacent the outlet of said divergent flow control member so that blood exiting from the upper, larger end of said flow control member passes adjacent said flange, said flange being substantially normal to said axis;

blood flow direction control means above said conical divergent flow control member for receiving arterial blood therefrom and to radially and circumferentially direct arterial blood flow within said body so that the arterial blood substantially fills said body;

said blood flow direction control means comprising a plurality of curved vanes secured to said flange and positioned at the outlet of said conical flow control member, said curved vanes being curved in a direction around said axis;

a chamber within said body above said blood flow control direction control means to receive gas separated from arterial blood flow, an outlet valve on said chamber to release gas from said chamber;

a blood filter member having an inlet side and an outlet side, said blood filter member being positioned within said hollow body so that its inlet side is towards said chamber and its inlet side receives blood which has already passed through said blood flow direction control means; and an outlet from said body below said flow direction control means to receive arterial blood from the outlet of said filter and to discharge arterial blood with reduced gas content from said separator.

19. An arterial blood-gas separator comprising:
a hollow body, said hollow body having an inlet and an outlet;

a stationary upwardly divergent flow control member positioned fixed within said body and connected to said inlet to receive arterial blood flow through said inlet for causing a reduction in flow velocity as the arterial blood flows upward in said upwardly divergent flow control member to substantially fill the interior of said hollow body;

blood flow direction control means above said divergent flow control member for receiving arterial blood therefrom, said blood flow direction control means comprising a plurality of flow deflectors that convert the generally axially directed blood flow upward in said divergent flow control member to tangential flow to phase-separate gases from the blood with the generally tangential flow of the arterial blood being submerged in the substantially arterial blood filled hollow body;

a chamber within said body above said blood flow direction control means to receive gas separated from the blood flow;

a filter having an inlet side and an outlet side positioned within said body between said arterial blood flow direction control means and said outlet with its inlet side towards said chamber so as to filter air bubbles out of arterial blood flow which is passing to said outlet from said body after centrifugal separation of gas from the arterial blood flow; and an outlet from said body below said flow direction control means and on the outlet side of said filter to discharge arterial blood with reduced gas content from said separator.

20. The directed flow bubble trap and arterial blood filter of claim 19 wherein said blood filter is formed of nylon filamentary fabric which has openings therein in the range of 20 to 60 microns.

21. An arterial blood-gas separator comprising:
a hollow body, said hollow body having an inlet and an outlet;
a gas release valve positioned at the top of said body to permit release of accumulated gas from the top of said body;
a stationary upwardly divergent flow control member secured within said body and connected to said inlet to receive arterial blood flow through said inlet for causing a reduction in flow velocity as the arterial blood flows upward in said upwardly divergent flow control member to substantially fill the interior of said hollow body;
blood flow direction control means above said divergent flow control member for receiving arterial blood therefrom, said blood flow direction control means comprising a plurality of flow deflectors that convert the generally axially directed blood flow upward in said divergent flow control member to tangential flow to phase-separate gases from the blood to permit the gases to rise in the body to be released from the body while the blood is in generally tangential flow in the substantially arterial blood filled hollow body while moving towards the outlet thereof.

22. The blood-gas separator of claim 21 wherein said gas release valve has a plug therein which is sealing against a shoulder, and said plug can be forced off of said shoulder by application of a tool to said plug.

23. The blood-gas separator of claim 21 wherein said gas release valve is a Luer cap removably attached to a Luer fitting positioned at the top of said hollow body.

24. The blood-gas separator of claim 21 wherein said gas release valve is a check valve positioned at the top of said body to permit release of accumulated gas but prevent retrograde flow into the housing.

25. The blood-gas separator of claim 24 wherein said check valve has a tube connected at the outlet thereof for discharge of gas from the top of said separator to an oxygenator.

26. A directed flow bubble trap and arterial blood filter comprising:
a housing;
inlet means for permitting the upward inlet flow of arterial blood into said housing to substantially fill said housing, said inlet means including an upwardly directed divergent flow control member fixed in said housing for causing a reduction in flow velocity as the arterial blood flows upward in said upwardly divergent flow control member for reducing blood velocity so that blood velocity at the top of said upwardly divergent flow control member in said housing is lower than in the entrance to said inlet means;
a plurality of vanes positioned at the top of and secured with respect to said divergent flow control member to convert the generally axially directed blood flow upward in said divergent flow control member to tangential flow around said housing to phase-separate gases from the arterial blood;
a low flow velocity volume in the top of said housing above said divergent flow conrol member and above said vanes so that air bubbles released from the tangentially moving arterial blood can separate upwardly into the low flow velocity volume, said housing top having an outlet valve therein for the release of gas collected within the top of said housing;
a blood filter member in said housing, said blood filter member having inlet and outlet sides and positioned around said upwardly divergent flow control member so that arterial blood leaving said upwardly divergent flow control member flows downward and reaches said inlet side of said filter member and air bubbles on the inlet side of said filter member and air bubbles on the inlet side member can rise into said housing top; and
an arterial blood outlet on said housing, said arterial blood outlet being connected to said housing so that it is positioned on the outlet side of said filter member to receive therefrom gas-separated and filtered arterial blood.

27. The directed flow bubble trap and arterial blood filter of claim 26 wherein said blood filter member has a filter material therein formed of nylon filamentary fabric which has openings therein in the range of 20 to 60 microns.

* * * * *